US012569177B2

(12) United States Patent
Frachi

(10) Patent No.: US 12,569,177 B2
(45) Date of Patent: Mar. 10, 2026

(54) SYSTEM FOR DETERMINING AN EMOTION OF A USER

(71) Applicant: Ovomind SA, Plan-les-Ouates (CH)

(72) Inventor: Yann Frachi, Marseilles (FR)

(73) Assignee: Ovomind SA, Plan-les-Ouates (CH)

( * ) Notice: Subject to any disclaimer, the term of this patent is extended or adjusted under 35 U.S.C. 154(b) by 606 days.

(21) Appl. No.: 17/753,920

(22) PCT Filed: Sep. 21, 2020

(86) PCT No.: PCT/IB2020/058762
§ 371 (c)(1),
(2) Date: Mar. 18, 2022

(87) PCT Pub. No.: WO2021/053632
PCT Pub. Date: Mar. 25, 2021

(65) Prior Publication Data
US 2022/0346682 A1 Nov. 3, 2022

(30) Foreign Application Priority Data
Sep. 20, 2019 (FR) ...................................... 1910395

(51) Int. Cl.
*A61B 5/0205* (2006.01)
*A61B 5/00* (2006.01)
(Continued)

(52) U.S. Cl.
CPC .......... *A61B 5/165* (2013.01); *A61B 5/02416* (2013.01); *A61B 5/7264* (2013.01)

(58) Field of Classification Search
CPC ... A61B 5/165; A61B 5/02416; A61B 5/7264; A61B 5/4035; A61B 5/02055;
(Continued)

(56) References Cited

U.S. PATENT DOCUMENTS

| | | | |
|---|---|---|---|
| 2003/0036685 A1* | 2/2003 | Goodman | .............. G16H 70/20 |
| | | | 600/300 |
| 2008/0214903 A1 | 9/2008 | Orbach | |

(Continued)

FOREIGN PATENT DOCUMENTS

KR 10-2016-0085577 A 7/2016

OTHER PUBLICATIONS

Dominguez-Jimenez et al., A Machine Learning Model for Emotion Recognition from Physiological Signals, Biomedical Signal Processing and Control, vol. 55, (2020), 11 Pages.
(Continued)

*Primary Examiner* — Carl H Layno
*Assistant Examiner* — Anh-Khoa N Dinh
(74) *Attorney, Agent, or Firm* — TraskBritt

(57) ABSTRACT

A method for calculating a numerical data pair representing an emotional state may include: —acquiring: a first series of physiological signals by at least one GSR and/or EDA electrodermal sensor, a second series of PPG physiological signals by a heart rate sensor, transmitting to a remote server the timestamped signals as well as an identifier of the acquisition device, processing each of the signals in order to characterize an $S_{arousal}$, $S_{valence}$ data pair, characterized in that: the processing of the first series of signals is of the EMD type over a sliding time window, to provide the first $S_{arousal}$ value of the pair, the processing of the second series of signals includes a step of band-pass filtering of frequencies comprised between 0.04 and 0.26 Hz and of peak detection and RR inter-peak time measurement, over the sliding time window, the to provide the second $S_{valence}$ value of said pair.

9 Claims, 1 Drawing Sheet

(51) Int. Cl.
    *A61B 5/024*       (2006.01)
    *A61B 5/0533*     (2021.01)
    *A61B 5/16*        (2006.01)

(58) Field of Classification Search
    CPC .......... A61B 5/0533; A61B 2562/0219; A61B
          5/0205; A61B 5/6843; A61B 5/7275;
          A61B 5/002; A61B 5/02028; A61B
          5/02438; A61B 5/1116; A61B 5/486;
          A61B 5/4875; A61B 5/681; A61B
          5/6826; A61B 5/721; A61B 5/7221; A61B
          5/7278; A61B 5/7282; A61B 5/7285;
          A61B 5/7405; A61B 5/741; A61B 5/742;
          A61B 5/7455; A61B 5/7475; A61B
          5/015; A61B 5/291; A61B 5/31; A61B
          5/369; A61B 5/374; A61B 5/377; A61B
          5/378; A61B 5/38; A61B 5/383; A61B
          5/384; A61B 5/4064; A61B 5/4088; A61B
          5/4806; A61B 5/4809; A61B 5/4812;
          A61B 5/4815; A61B 5/4818; A61B
          5/4842; A61B 5/6803; A61B 5/6814;
          A61B 5/72; A61B 5/7235; A61B 5/725;
          A61B 5/7267; A61B 5/0024; A61B
          5/0031; A61B 5/01; A61B 5/021; A61B
          5/14532; A61B 5/14551; A61B 5/1468;
          A61B 5/318; A61B 5/389; A61B 5/6817;
          A61B 5/6823; A61B 5/6846; A61B
          5/6898; A61B 5/7203; A61B 5/7225;
          A61B 5/7246; A61B 7/003; A61B 7/04
    See application file for complete search history.

(56) References Cited

U.S. PATENT DOCUMENTS

| | | | |
|---|---|---|---|
| 2011/0300847 A1* | 12/2011 | Quy ........................ | H04W 4/00 |
| | | | 455/419 |
| 2016/0345060 A1 | 11/2016 | Marci et al. | |
| 2019/0239795 A1 | 8/2019 | Kotake et al. | |
| 2023/0337961 A1* | 10/2023 | Šarlija .................. | A61B 5/4818 |

OTHER PUBLICATIONS

Gautam et al., A Data Driven Empirical Iterative Algorithm for GSR Signal Pre-Processing, 2018 26th European Signal Processing Conference, Sep. 3, 2018, 4 pages.
International Search Report for Application No. PCT/IB2020/058762 dated Oct. 14, 2022, 4 pages.
International Written Opinion for Application No. PCT/IB2020/058762 dated Oct. 14, 2022, 7 pages.

\* cited by examiner

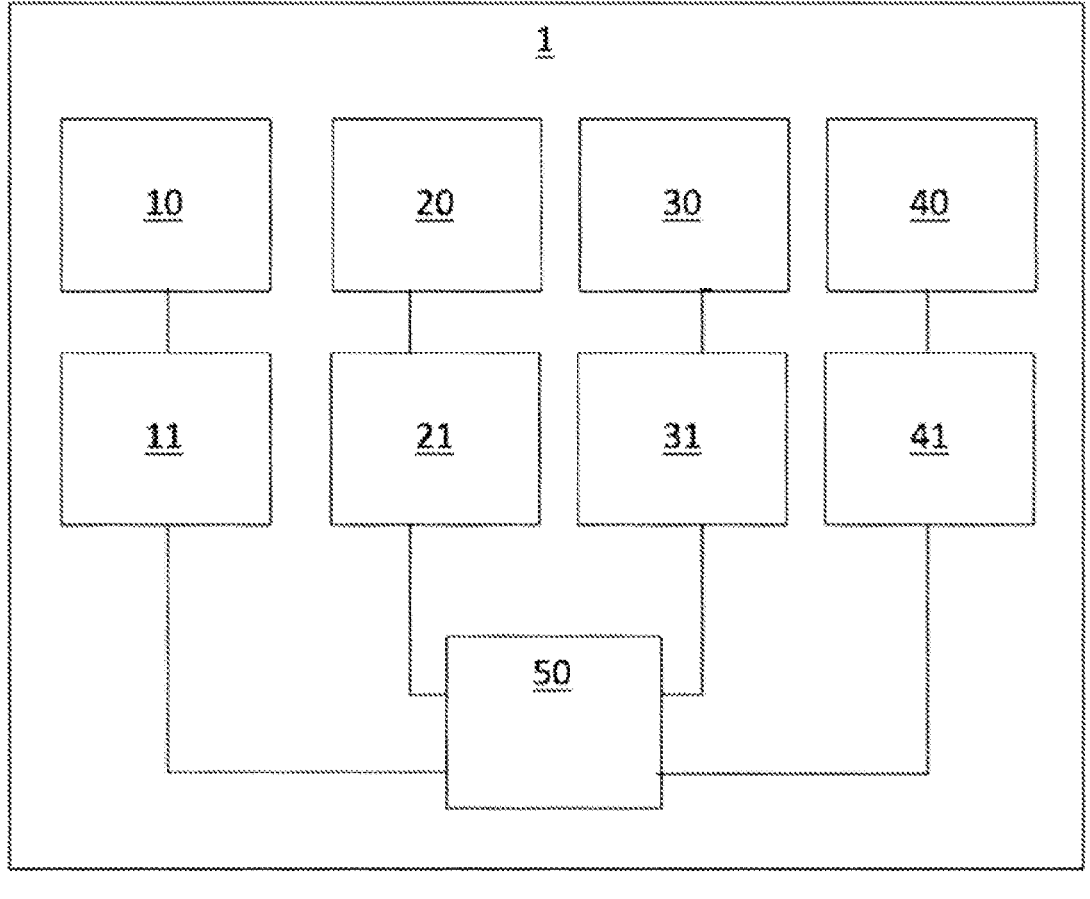

SYSTEM FOR DETERMINING AN EMOTION OF A USER

CROSS-REFERENCE TO RELATED APPLICATIONS

This application is a national phase entry under 35 U.S.C. § 371 of International Patent Application PCT/IB2020/058762, filed Sep. 21, 2020, designating the United States of America and published as International Patent Publication WO 2021/053632 A1 on Mar. 25, 2021, which claims the benefit under Article 8 of the Patent Cooperation Treaty to French Patent Application Serial No. 1910395, filed Sep. 20, 2019.

TECHNICAL FIELD

The present disclosure relates to the field of the detection of physiological activities of an individual, in particular, for capturing, identifying and analyzing the emotions of the individual in order to allow for automatic characterization, for example, with the aim of amplifying emotions in a person, or for interacting with an external interactive system providing an immersive experience for a user. For this purpose, it is known to make use of electrophysiological signals acquired by cutaneous sensors for concluding correlations with the emotional state.

BACKGROUND

It has long been known that the cutaneous or electrodermal conductance (for example)) can be dependent on the emotions of an individual (e.g., the polygraph or "lie detector"). Even if these devices make it possible to show that the cutaneous conductance varies, they cannot simply determine the type of emotions (or the valence) associated with the variation—is this variation associated with great joy (or more generally associated with a positive emotion) or with fear (or more generally associated with a negative emotion)?

The research in the field of the study of emotions is based in two main fields:

For some researchers, whose work focusses on dimensional aspects, the emotional states are governed by underlying factors such as the valence, the excitation, and the motivational state.

For other researchers, whose work focusses on the discrete analysis of emotions, each emotion has experimental, physiological and behavioral corollaries.

To Date, Five Methods Coexist:

The first method for capturing emotions is self-reporting—this method proposes that the emotions should be measured and evaluated by the person themselves.

The second method uses tools for measuring responses of the automatic nervous system (ANS). Different measurements of the activity of the automatic nervous system may operate independently of or in opposition to one another. The capturing of emotions by this means is achieved by way of studying physiological signals such as the electrodermal activity (EDA) and the heart rate (HR). However, this method requires a large number of measurements from different sources, and thus complicates the devices.

The third method involves calculating the response magnitude to an unexpected stimulus, in order to measure the valence in a specific context with a high-intensity stimulus. The magnitude is sensitive to the valence only in the context of a high-excitation stimulus. Thus this method is not suitable for the detection of a discrete emotional state or a lower excitation emotional state.

The fourth method is based on the study of the central nervous system (CNS) by means of an electroencephalogram (EEG) and brain imaging. This method requires heavy infrastructure and is not suitable for day-to-day use. The usage costs are significant, and the experiments are very invasive in nature, which may dissuade individuals from participating in them. These factors thus make these techniques difficult to control and validate.

The last method is based on the bodily behavior, which translates the body's response to the emotion (e.g., analysis of the voice or facial expression). Nonetheless, this latter method is complex to implement for daily use. Therefore, there is a need to allow for better detection of emotions, by means of a limited number of measurements (e.g., just one source of measurements), while allowing for reliable detection of the valence of emotions.

Korean Patent Application KR20160085577 is known, which describes an apparatus for determining a psychological state comprising: a bio-signal acquisition unit for acquiring a first bio-signal and a second bio-signal of a user generated by a first stimulus; and psychological state determination unit for extracting a first characteristic and a second characteristic by analyzing the first bio-signal and the second bio-signal and by determining the psychological state of the user on the basis of the first characteristic and the second characteristic. The first bio-signal and the second bio-signal are bio-signals that indicate changes in the automatic nerves measured by different bio-sensors.

U.S. Patent Application 2008214903 is also known, describing a solution that implements one or more portable sensor modules for transmitting the physiological parameter(s). One or more emitters wirelessly transmit signals that report the values of one or more physiological parameters to a mobile monitor. The mobile monitor comprises a processor that processes the signals received from the emitter, in real time, using expert knowledge. A device provides one or more indications on the results of the processing. The invention also relates to portable mobile sensors for use in the system of the invention. The method involves obtaining the values of the physiological parameters of the user from one or more portable sensor modules. The signals that report the values of the physiological parameter(s) are transmitted wirelessly to a mobile monitor. The signals are processed in real time by means of expert knowledge, and one or more indications of results of the processing are provided to the mobile unit.

U.S. Patent Application 2019239795 describes a method comprising the following steps: storing information on an emotion of the subject, and information on an activity of the subject; generating learning data representing a relationship between the stored information on the emotion of the subject and the stored information on the activity of the subject, and storing learning data in a memory, after the learning data are generated, for a current emotion of the subject, on the basis of information relating to a current activity of the subject obtained by the obtention unit, and the learning data stored in the memory; and providing assistance for driving the vehicle, on the basis of the current emotion. In the same way, the invention relates to apparatuses for controlling the production line, and healthcare assistance, the apparatuses making it possible to provide production line control and healthcare assistance on the basis of the estimated emotion. The apparatus estimates the emotional variations of the subject, by means of regression equations, and variations in characteristics of the measurement data elements, or of the electrical activity of the heart (H), of the activity of the cutaneous potential (G), of the eye movement (EM), of the movement (BM), and of the amount of activity (Ex) of the subject measured by the measurement device.

U.S. Patent Application 2016345060 describes the measurement, by means of sensors, of the responses of an individual to the content during a first time period, the determination of response classifications on the basis of a comparison of the responses and the respective thresholds, the determination of a first metal classification of the individual based on the combination of the response classifications, the determination of a baseline during the first time period, measuring additional responses to the content during a second time period, determining additional response classifications on the basis of a comparison of the additional responses at respective additional thresholds, adjusting the baseline on the basis of the additional responses in the second time period.

The Following Articles are Also Known:

A machine learning model for emotion recognition from physiological signals Author J. A. Dominguez-Jiménez, K. C. Campo-Landines, J. C. Martinez-Santos, E. J. Delahoz, S. H. Contreras-Ortiz; Universidad Tecnológica de Bolivar, Km 1 Via Turbaco, Cartagena de Indias, Colombia; Received 6 Dec. 2018, Revised 26 Jun. 2019, Accepted 7 Aug. 2019, Available online 3 Sep. 2019.

A data driven empirical iterative algorithm for GSR signal pre-processing auteurs Arvind Gautam, Neide Simoes-Capela, Giuseppina Schiavone, Amit Acharyya, Walter De Raedt, Chris Van Hoof; published 2018 Sep. 3 in 2018 26th European Signal Processing Conference (EUSIPCO), Pages 1162-1166.

The known solutions do not make it possible to provide a signal that is actually representative of the emotional state, taking into account underlying factors such as the valence and the arousal level, which are, however, decisive for a relevant characterization of the emotional state, in an automatic manner and without the intervention of a person trained in the psychological evaluation of the emotional state, or to provide reliable, robust and reproducible information.

Today, no systems exist in the form of a connected bracelet that makes it possible to identify, in real time, the emotional state from physiological data (cardiac activity, referred to as PPG for photoplethysmography, electrodermal conductance, referred to as GSR for galvanic skin response) Indeed, the existing devices/systems use classification algorithms (automatic learning) that require a frequency analysis of the cardiac activity over a period of the order of 5 minutes.

Moreover, the performance of current classification algorithms is greatly limited by emotional induction protocols that are too specific, and by methods for emotional labelling of physiological data from subjective measurements (questionnaires, Likert scales, etc.). Indeed, the variations among individuals in the subjective representation of emotions, coupled with the variations among individuals in the quality of the physiological signals, do not make it possible to classify the emotions in a robust and non-contextualized manner.

Finally, the physiological expression of emotions may not be evaluated too specifically, as most research laboratories attempt to do, because a group of emotions may produce similar physiological responses. For example, the reaction of surprise, or sexual attraction, produce GSR signals having similar characteristics. It is preferable to understand the physiological expression of emotions by taking into account the actual functioning of the automatic nervous system, which plays a fundamental role in the adjustment to emotions. The two activating and inhibiting branches of the automatic nervous system (the sympathetic and parasympathetic nervous systems, respectively) act in an antagonistic manner, as a dynamic balance. This balance makes it possible to understand the different emotional groups, and can be characterized proceeding from non-invasive measures.

BRIEF SUMMARY

In order to overcome these disadvantages, the present disclosure relates generally to a computer-implemented method for calculating a digital data pair representing an emotional state, the method comprising:

acquiring:

a first series of physiological signals by at least one electrodermal activity (EDA) sensor;

a second series of physiological signals by photoplethysmography (PPG); photoplethysmography is a non-invasive technique for vascular functional exploration used, in particular, by connected watches and bracelets in order to measure the heart rate of the wearer of the watch;

transmitting to a remote server the timestamped signals as well as an identifier of the acquisition device; and processing each of the signals in order to characterize a data pair, wherein the processing of the first series of signals is of the EMD (empirical mode decomposition) type over a sliding time window, the result of which provides the first value of the pair (arousal); and the processing of the second series of signals comprises a step of band-pass filtering of frequencies between 0.04 and 0.26 Hz and of peak detection and RR inter-peak time measurement, over the sliding time window, the result of which provides the second value of the pair (valence).

Preferably, the series of GSR and PPG data are time-stamped and transmitted in the form of digital messages to a computer that performs the calculations for calculating the $S_{arousal}$, $S_{valence}$ values in real time.

Advantageously, the series of GSR and PPG data are stored in calculation buffers, including the buffer memories for the application of sliding time window processing.

According to a variant, the method comprises a step of band-pass filtering (4th order Butterworth) of the GSR signal having a passband of between 0.05 and 1 HZ.

Advantageously, the processing for the determination of the signal $S_{Arousal}$ is performed over a time window of from 15 to 25 seconds, starting from the normalized spectral power of the GSR signal calculated on the band 0.045-0.25 Hz.

According to another variant, the method comprises a step of band-pass filtering (4th order Butterworth) of the PPG signal having a passband of between 0.5 and 5 Hz.

According to a particular embodiment, the method further comprises a viewing step, comprising ordering the display of a graphical form, a first parameter of which depends on the value of the signal $S_{arousal}$, and a second parameter of which depends on the value of the signal $S_{valence}$.

Advantageously, the first parameter includes the size, the thickness of the contour, or the form factor, and the second parameter includes the color and the orientation of the main axis of the graphical form.

According to another advantageous embodiment, the method comprises a preceding step of supervised learning, in which includes presenting, to a panel of people equipped with a device for acquisition of the physiological signals GSR and/or EDA and PPG, a plurality of experimental plans formed by a succession of video sequences that are each associated with a numerical identifier ID (t), and recording the pairs of signals $S_{arousal}$ and $S_{valence}$ and their development over time, for each of the members of the panel, and Once the level of valence has been estimated, it is then possible to verify the level of arousal, by controlling, in the spectral domain, the level of physiological activation, using a GSR signal, in order to deduce therefrom, in real time, the emotional state of the individual, and to communicate this to the multimedia system with which the individual interacts.

It is possible to characterize the emotional state according to the following table:

TABLE 1

| | $S_{valence}+$ | | | | | |
|---|---|---|---|---|---|---|
| + $S_{arousal}$ − | | NERVOUS | TENSE | ALERT | EXCITED | |
| | UPSET | | | | | |
| | SAD | | | | | HAPPY |
| | DEPRESSED | | | | CONTENT | |
| | | ANNOYED | | SERENE | | |
| | | RELAXED | | | | | then in injecting the structured data ($S_{arousal}$ and $S_{valence}$ (t); ID (t)) into a neural network in order to develop a characterization model.

BRIEF DESCRIPTION OF THE DRAWING

Embodiments of the present disclosure are described below, by way of non-limiting example, with reference to the accompanying drawing, in which:

FIG. 1 illustrates an embodiment of a device for acquiring electrophysiological signals.

DETAILED DESCRIPTION

The disclosure provides, automatically and without human intervention, a pair of digital signals $S_{arousal}$ and $S_{valence}$, which are representative of the emotional state of a person.

The efficient recognition of emotions from human physiological activity may make use of a simple emotional model. Indeed, the emotions can be projected in a multidimensional space, the more common being the valence/arousal plane. The valence level represents the positivity and the negativity of an emotion, while the arousal level describes the intensity of the emotion. These two emotional components are expressed at the physiological level.

In the event of stress, the sympathetic nervous system predominates, and leads to an increase in the level of physiological arousal. An acceleration of the heart rate or an acceleration of the interbeat interval (IBI) is characteristic of this state. In contrast, at rest the parasympathetic nervous system is activated, resulting in a reduction of the state of physiological arousal and of the heart rate. Furthermore, the alternation of accelerations and decelerations of the heart rate becomes regular and coherent (state of cardiac coherence) in states of wellbeing, calm or self-control (positive emotional valence), while in states of stress, anxiety or anger (negative emotional valence), the tachogram corresponding to the pair $S_{arousal}$ and $S_{valence}$ becomes irregular, its trace chaotic, and its magnitude will reduce.

Extracting, from the PPG signal, the level of coherence of the heart rate, makes it possible to obtain a robust indicator of the level of emotional valence, and to calculate dynamic thresholds beyond which the level of valence changes significantly.

In the event of a stress, the sympathetic nervous system predominates, and leads to an increase in the level of physiological arousal. An acceleration of the heart rate is characteristic of this state. In contrast, at rest the parasympathetic nervous system is activated, resulting in a reduction of the state of physiological arousal and of the heart rate. Furthermore, the alternation of accelerations and decelerations of the heart rate becomes regular and coherent (state of cardiac coherence) in states of wellbeing, calm or self-control (positive emotional valence), while in states of stress, anxiety or anger (negative emotional valence), the tachogram becomes irregular, its trace chaotic, and its magnitude will reduce.

Extracting, from the PPG signal, the level of coherence of the heart rate, makes it possible to obtain a robust indicator of the level of emotional valence, and to calculate dynamic thresholds beyond which the level of valence changes significantly.

Once the level of valence has been estimated, it is then possible to verify the level of arousal, by controlling, in the spectral domain, the level of physiological activation, using a GSR signal, in order to deduce therefrom, in real time, the emotional state of the individual, and to communicate this to the multimedia system with which the individual interacts:

Device for Acquiring Electrophysiological Signals

The acquisition device has a cutaneous contact surface that comprises the sensors. It can be provided at the surface of a support such as a bracelet intended to be worn on the arm or on the ankle, the back of a watch, or indeed of a patch that can be affixed to the user's skin.

The cutaneous contact surface (1) of the acquisition device comprises a plurality of sensors (10, 20, 30, 40) intended for obtaining measurements of physiological signals associated with the user's emotions, for example:

a sensor (10), which is suitable for measuring a heart rate of the user;

a sensor (20), which is suitable for measuring the electrical conductivity observed at the surface of the skin of the user, and providing a signal that is representative of the electrodermal activity (EDA);

a sensor (30), which is suitable for measuring the surface temperature of the skin;

a sensor (40), which is formed by a triaxial or polyaxial accelerometer, such as a 9-axis inertial module, suitable for allowing for the measurement of movements on a limb of the user.

The sensor (20) provides a signal representative of a passive or endosomatic parameter that corresponds to the skin conduction level (SCL), or of an active or exosomatic parameter that corresponds to the level of the skin conductance response (SCR). These parameters make it possible to determine the electrodermal activity (EDA), which can be traced back to the characteristics of the epidermal membrane, and the sweat gland activity of the eccrine type, under the control of the autonomous and central nervous systems.

Two recording methods are distinguished.

The first method, referred to as endosomatic, conveys the potential differences generated by the cutaneous membranes, and results in the measurement of the electrodermal potential. In this case, the sensor (20) is a sensor for sensing the conductivity of the skin, associated with a current/voltage converter, for example, a sensor for sensing the resistivity of the skin, provided with a pair of stainless steel electrodes.

The second method, referred to as exosomatic, conveys the variations in a current applied to the skin, the characteristics of which can result in the measurement of various electrodermal signals, including the measurement of the cutaneous conductance, which is the most commonly used in the literature. Each of the electrodermal signals is divided into a tonic component and a phasic component.

The first identifies the slow variations of the electrodermal signal, while the second corresponds to the fast variations of the signal, commonly referred to as electrodermal responses. Various measuring parameters, such as the frequency, the latency, or the amplitude of the electrodermal responses can be extracted from these phasic measurements. The origins, as well as the variability, of the measuring parameters of the electrodermal activity make this activity a measurement that is sensitive to changes in our environment, and to different mental processes under the control of the central nervous system, such as emotion, motivation, or indeed attention, and mental stress.

Each sensor (10, 20, 30, 40) is associated with a pre-processing circuit (11, 21, 31, 41) that optionally performs analog processing (pre-amplification, filtration, provision of an excitation signal) and digitization processing (sampling, optional digital filtering, storage in a buffer memory, etc.) for providing a computer (50) with digital signals that are exploited to determine the pair of values representing the emotional state.

Processing of Physiological Signals

The signals provided by the sensor (40) are sampled at a frequency of 64 Hz and filtered in amplitude and frequency in order to suppress the aberrant signals. These signals constitute environmental information that completes the signals associated with emotions, for example, in order to provide a context of mode of movement and/or fall.

The signals provided by the electrical conductivity sensor (20) are sampled at a frequency of 8 Hz and then processed for the calculation of the arousal score and the level of vigilance.

The signals provided by the sensor (10) for sensing the user's heart rate are sampled at a frequency of 50 Hz and used by the computer (50) for determining the valence score, as well as for biometric recognition, and for estimating the stress level.

The sensor (30) for measuring the temperature of the skin is sampled at a low frequency, of the order of 1 HZ, and completes the information allowing for characterization of the emotional state.

Particular Embodiment

One embodiment involves equipping the patient with a wireless connected bracelet equipped with three physiological sensors (just one sensor may suffice) that measure the electrodermal conductance (referred to as GSR for galvanic skin response) at a rate of 8 Hz, the cardiac activity (referred to as PPG for photoplethysmography) at a rate of 50 Hz, the body temperature (referred to as SKT for skin temperature) at a rate of 1 Hz, and one or more accelerometric sensors (referred to as ACC) at a rate of 50 Hz is used for synchronously recording the data and the corresponding time stamps.

The GSR and PPG data are transmitted to a mobile terminal that performs the calculations for real-time identification of the emotional state. The GSR and PPG data are stored in calculation buffers, the durations of which vary depending on the variables calculated.

In each buffer memory, the processing of the signal is performed prior to the extraction of the different variables used for the analysis of the identification of the emotional state:

GSR signal: Band-pass filtering (4th order Butterworth) is applied to the signal, at a passband of 0.05-1 Hz.

PPG signal: Band-pass filtering (4th order Butterworth) is applied to the signal, at a passband of 0.5-5 Hz.

The variables used for the analysis of the identification of the emotional state are then extracted from the processed signals. The variable Arousal is obtained in a computer buffer memory of 20 seconds, proceeding from the normalized spectral power of the GSR signal calculated on the band 0.045-0.25 Hz by means of a Hilbert-Huang transform.

Example of Processing

The variable Mdiff is recorded in a compute buffer of 2 seconds, proceeding from the average of the absolute value of the first derivative of the GSR signal.

The variable Valence is obtained in a compute buffer of 60 seconds, by calculating the cardiac coherence ratio. In order to achieve this, peaks in the PPG signal are detected proceeding from a dedicated function, in order to deduce therefrom the peak-to-peak time intervals, referred to as RR intervals. Then, the heart rate, referred to as BPM, is calculated from the RR intervals.

From the BPM signal, the maximum peak of the power spectrum is identified on the band 0.04-0.26 Hz (the frequency range within which the coherence can be observed). The power of the peak, referred to as Peak Power, is then determined by calculating the integral over a window 0.030 Hz wide, centered around the peak. The total power over the band 0.0033-0.4 Hz of the BPM signal, referred to as Total Power, is then calculated.

The normalized valence level is obtained by the following calculation:

Equation 1

$$\text{Valence} = \frac{\text{Peak Power}}{\text{Total Power} - \text{Peak Power}} \quad (1)$$

Every second, the new GSR and PPG values recorded by the bracelet make it possible to calculate the new Arousal, Mdiff and Valence values.

Mdiff is stored in the memory at the last minute, in order to allow for a dynamic calibration of the system for detecting punctual variations of the physiological arousal level. A weighting coefficient is applied to these calibration data in order to make the contribution of the most recent values of more significance during the calibration. It is then possible to calculate the dynamic thresholds that make it possible to classify, respectively, the variable Mdiff. The calculation of the thresholds can be explained in the following manner:

Equation 2

$$Threshold_{(t)} = \frac{\text{Max}\left(Mdiff\left[\begin{matrix} x_1 \\ \vdots \\ x_n \end{matrix}\right]\right) + \text{Average}\left(Mdiff\left[\begin{matrix} x_1 \\ \vdots \\ x_n \end{matrix}\right]\right)}{2} \quad (2)$$

With $Threshold_{(t)}$ the value of the dynamic threshold at the timepoint t, and $$Mdiff\left[\begin{matrix} x_1 \\ \vdots \\ x_n \end{matrix}\right]$$

the values of the variable Mdiff over the entire duration of the calibration period.

Every second, a new Threshold value is obtained and compared with Mdiff. If Mdiff is greater than its threshold value, then an emotional reaction is detected.

Learning the Characterization Criteria

In order to construct a characterization model, the disclosure describes a variant that implements a preparatory step of supervised learning.

This solution comprises proposing, to a panel of users equipped with a device for acquisition of the above-mentioned physiological data, experimental plans formed by a succession of video sequences that are each associated with a numerical identifier ID (t), and recording the pairs of signals $S_{arousal}$ and $S_{valence}$ and their development over time, for each of the members of the panel.

The structured data ($S_{arousal}$ and $S_{valence}$ (t); ID (t)) for each of the members of the panel are then injected into a neural network in order to develop a characterization model.

The participants will be equipped with a connected bracelet according to the disclosure, equipped with three physiological sensors that measure the cardiac activity (referred to as PPG for photoplethysmography), the body temperature (referred to as SKT for skin temperature), and electrodermal conductance (referred to as GSR). The bracelets communicate with a portable acquisition computer that makes it possible to synchronously record the data and the corresponding timestamping at an acquisition frequency of 50 Hz, 1 Hz and 4 Hz for the PPG, the SKT and the GSR, respectively, for the connected bracelet or connected watch and at an acquisition frequency of 64 Hz, 4 Hz and 4 Hz for the PPG, the SKT and the GSR.

A virtual reality system HTC Vive will be used to display the stimuli selected in order to induce an emotional reaction, and makes it possible to have an additional immersion (new protocol compared with emotional stimulation).

Experimental Design

For each participant, the data are recording in one single session of twenty minutes. The experiment plan is: Sn (participants)*V6 (six emotional videos).

Each Video Corresponds to an Emotional Extreme

Video 1: Rest (40 s)—Phase of emotional induction of the sadness type (30 s)—Post-effect (30 s)

Video 2: Rest (40 s)—Phase of emotional induction of the joy type (30 s)—Post-effect (30 s)

Video 3: Rest (40 s)—Phase of emotional induction of the disgust type (30 s)—Post-effect (30 s)

Video 4: Rest (40 s)—Phase of emotional induction of the fear type (30 s)—Post-effect (30 s)

Video 5: Rest (40 s)—Phase of emotional induction of the neutral type (30 s)—Post-effect (30 s)

Video 6: Rest (40 s)—Phase of emotional induction of the relaxation type (30 s)—Post-effect (30 s)

The rest phase will constitute a reference period for initializing the calculation of the physiological variables. For each participant, the order of presentation of the videos will be random, in order to avoid any effect of order. Moreover, in order to enrich the dataset, two videos will be available for the emotions of the fear and joy type. For each participant, the choice of the video used for each of these two emotions will be random.

Data Acquisition Procedure

Each participant is first equipped with one or more connected bracelets, and a virtual reality system allowing them to isolate themselves from external stimulations and to optimize their attention focus. The experimenter then checks the quality of the physiological signals. Each participant will have the general instruction to view six videos of a period of 30 seconds. During the 40 seconds preceding the video, and the 30 seconds following the video, the instructions given will be to remain calm and still. When all the videos have been viewed, the experimenter helps the participant to remove the virtual reality headset and the bracelet, and then carries out a debrief in order to check that everything has gone well.

Analysis of the Data

For each participant, the physiological data recorded will be pre-processed in the following manner:

For the PPG signal, the signal jumps will be corrected by means of a dedicated function. Band-pass filtering (4th order Butterworth) will then be applied to the signal, at a passband of 0.5-5 Hz, and then the signal will be normalized by means of a Hilbert transform, and smoothed by means of a Gaussian window of 16 seconds. With regard to the SKT signal, band-pass filtering (4th order Butterworth) will be applied to the signal, at a cutoff frequency of 0.05 Hz. Finally, band-pass filtering (4th order Butterworth) will be applied to the GSR signal, at a passband of 0.05-3 Hz. All these variables will constitute the input data of the emotional classification algorithms.

Graphical Representation of the Processing Results

Every second, the variables obtained are represented by the system for displaying the emotional state detected (referred to as overlay), in the following manner:

The diameter of the circle corresponds to the normalized value of the value $S_{Arousal}$. The greater the diameter, the more the arousal level is raised.

The color of the circle corresponds to the normalized value of the value $S_{Valence}$. When the color tends toward green, the valence level is higher. When the color tends toward red, the valence level is weaker.

When an emotional reaction is detected proceeding from the development parameter Mdiff, the contour of the circle becomes animated. The heart rate value updates at the center of the circle.

The emotional state is communicated to the multimedia system with which the individual interacts. It is important to note that the dock/mobile provides for the updating of the bracelet on the one hand, and methods for calculation of values and detection levels on the other hand, via an Internet connection.

Applications

The method according to the disclosure makes it possible to provide control signals for guiding an item of equipment such as a robot, in particular, an empathetic robot, or for controlling functional parameters of an electronic item of equipment, such as the sound level, light level, rhythm, etc.

These signals also make it possible to control the adjustment of the speed of an individual/public transport vehicle, and the management of security officers, control officers, pilots, and drivers.

The invention claimed is:

1. A method for calculating a digital data pair representing an emotional state, comprising:

using an acquisition device configured to obtain measurements of physiological signals via a plurality of sensors, acquiring:

a first series of physiological signals by at least one GSR and/or EDA electrodermal sensor; and a second series of PPG (photoplethysmography) physiological signals by a heart rate sensor;

transmitting, via the acquisition device, time stamped signals and an identifier associated with the time stamped signals to a remote server;

processing each of the timestamped signals to characterize an $S_{arousal}$, $S_{valence}$ data pair, wherein:

processing of the first series of physiological signals is of an EMD (empirical mode decomposition) type over a sliding time window, a result of which provides a first $S_{arousal}$ value of the digital data pair;

processing of the second series of PPG physiological signals comprises a step of band-pass filtering of frequencies between 0.04 and 0.26 Hz and of peak detection and RR inter-peak time measurement, over the sliding time window, a result of which provides a second $S_{valence}$ value of the digital data pair; and providing a control signal to control one or more of a multimedia system, a robot, and a transport vehicle based on the emotional state.

2. The method of claim 1, wherein data relating to the first series of physiological signals and the second series of PPG physiological signals is timestamped and transmitted as digital messages to a computer that performs the calculations for calculating the $S_{arousal}$, $S_{valence}$ values in real time.

3. The method of claim 1, wherein data relating to the first series of physiological signals and the second series of PPG physiological signals is stored in calculation buffers, including buffer memories for application of sliding time window processing.

4. The method of claim 1, further comprising band-pass filtering of a GSR signal having a passband of between 0.05 and 1 Hz.

5. The method of claim 4, wherein processing for determination of a signal $S_{arousal}$ is performed over a time window of from 15 to 25 seconds, starting from normalized spectral power of the GSR signal calculated on the band 0.045-0.25 Hz.

6. The method of claim 1, further comprising band-pass filtering of a PPG signal having a passband of between 0.5 and 5 Hz.

7. The method of claim 1, further comprising a viewing step including providing, to an electronic display device, a graphical form of a first parameter of which depends on the value of a signal $S_{arousal}$, and a second parameter of which depends on the value of a signal $S_{valence}$.

8. The method of claim 7, wherein the first parameter includes a size, a thickness of a contour, or form factor, and the second parameter includes color and orientation of the main axis of the graphical form.

9. The method of claim 1, further comprising a preceding step of supervised learning including presenting, to a panel of people equipped with a device for acquisition of the physiological signals GSR and/or EDA and PPG, a plurality of experimental plans formed by a succession of video sequences that are each associated with a numerical identifier ID (t), and recording the digital data pairs of signals $S_{arousal}$ and $S_{valence}$ and their development over time, for each member of the panel of people, and then injecting structured data ($S_{arousal}$ and $S_{valence}$ (t); ID (t)) into a neural network to develop a characterization model.

* * * * *